US009827174B2

(12) United States Patent
Levine et al.

(10) Patent No.: US 9,827,174 B2
(45) Date of Patent: Nov. 28, 2017

(54) CLOSED SYSTEM MOUTHPIECE WITH LIGHT AND HEAT GENERATION TO ACTIVATE A FORMULATION TO INCREASE ITS VOLUME

(71) Applicant: JBL RADICAL INNOVATIONS, LLC, New York, NY (US)

(72) Inventors: Jonathan B. Levine, Purchase, NY (US); Robert E. Theroux, Palm Coast, FL (US); Howard Matthews, Ontario (CA); Jordan Goncalves, Brooklyn, NY (US)

(73) Assignee: JBL RADICAL INNOVATIONS, LLC

( * ) Notice: Subject to any disclaimer, the term of this patent is extended or adjusted under 35 U.S.C. 154(b) by 0 days.

(21) Appl. No.: 15/427,480

(22) Filed: Feb. 8, 2017

(65) Prior Publication Data

US 2017/0143596 A1    May 25, 2017

Related U.S. Application Data

(63) Continuation-in-part of application No. 13/956,787, filed on Aug. 1, 2013, now Pat. No. 9,572,645.

(51) Int. Cl.
*A61K 8/04*     (2006.01)
*A61K 8/49*     (2006.01)
(Continued)

(52) U.S. Cl.
CPC ............ *A61K 8/046* (2013.01); *A61C 19/063* (2013.01); *A61C 19/066* (2013.01); *A61F 7/12* (2013.01);
(Continued)

(58) Field of Classification Search
CPC ............ A61K 8/046; A61K 8/58; A61Q 11/00
See application file for complete search history.

(56) References Cited

U.S. PATENT DOCUMENTS 5,674,182 A    10/1997 Suzuki et al.
6,607,387 B2    8/2003 Mault
(Continued)

FOREIGN PATENT DOCUMENTS

WO    WO0162211 A2 *  8/2001 ............ A61K 8/046

OTHER PUBLICATIONS

Translation of WO 0162211 by Bressler et al.*
(Continued)

*Primary Examiner* — Mike M Dollinger
*Assistant Examiner* — Christina Wales
(74) *Attorney, Agent, or Firm* — H. Jay Spiegel

(57) ABSTRACT

A formulation starts as a gel and transforms into a foam under influence of light and heat to expand out into the oral cavity of a user for advantageous health benefits. A closed system mouthpiece includes light and heat generation to activate the formulation to increase its volume. Application of heat above a threshold temperature causes the gel to transform into foam and expand out of the mouthpiece and into the oral cavity. With the foam so dispersed within the oral cavity, activation of a light source embedded within the mouthpiece enhances the bacteria killing properties of the now foam material. The foam spreads onto the tongue of the user as well and acts to kill any damaging bacteria found there. As a result, the pH balance of the mouth is restored to a neutral level in the range of 6.75 to 7.25 or maintained at that pH level.

19 Claims, 7 Drawing Sheets

(51) Int. Cl.

| | |
|---|---|
| *A61K 8/19* | (2006.01) |
| *A61K 8/22* | (2006.01) |
| *A61K 8/34* | (2006.01) |
| *A61K 8/86* | (2006.01) |
| *A61K 8/81* | (2006.01) |
| *A61K 8/44* | (2006.01) |
| *A61K 8/25* | (2006.01) |
| *A61K 8/31* | (2006.01) |
| *A61K 8/64* | (2006.01) |
| *A61Q 11/00* | (2006.01) |
| *A61F 7/12* | (2006.01) |
| *A61C 19/06* | (2006.01) |
| *A61F 7/00* | (2006.01) |
| *A61N 5/06* | (2006.01) |
| *A61C 13/15* | (2006.01) |

(52) U.S. Cl.
CPC ............... *A61K 8/19* (2013.01); *A61K 8/22* (2013.01); *A61K 8/25* (2013.01); *A61K 8/31* (2013.01); *A61K 8/34* (2013.01); *A61K 8/345* (2013.01); *A61K 8/347* (2013.01); *A61K 8/44* (2013.01); *A61K 8/4926* (2013.01); *A61K 8/645* (2013.01); *A61K 8/8176* (2013.01); *A61K 8/86* (2013.01); *A61Q 11/00* (2013.01); *A61C 19/003* (2013.01); *A61F 2007/0017* (2013.01); *A61K 2800/522* (2013.01); *A61K 2800/524* (2013.01); *A61K 2800/596* (2013.01); *A61K 2800/805* (2013.01); *A61K 2800/81* (2013.01); *A61K 2800/87* (2013.01); *A61K 2800/92* (2013.01); *A61N 5/0624* (2013.01); *A61N 2005/0606* (2013.01)

(56) References Cited

U.S. PATENT DOCUMENTS

| | | | |
|---|---|---|---|
| 7,223,270 | B2 | 5/2007 | Altshuler et al. |
| 7,223,281 | B2 | 5/2007 | Altshuler et al. |
| 7,329,273 | B2 | 2/2008 | Altshuler et al. |
| 7,329,274 | B2 | 2/2008 | Altshuler et al. |
| 7,354,448 | B2 | 4/2008 | Altshuler et al. |
| 7,422,598 | B2 | 9/2008 | Altshuler et al. |
| 2004/0005277 | A1* | 1/2004 | Willison ............... A61C 19/06 424/53 |
| 2004/0010299 | A1 | 1/2004 | Tolkoff et al. |
| 2005/0113654 | A1 | 5/2005 | Weber et al. |
| 2008/0032252 | A1 | 2/2008 | Hayman et al. |
| 2008/0233541 | A1 | 9/2008 | De Vreese et al. |
| 2009/0017422 | A1 | 1/2009 | Creamer |
| 2009/0132011 | A1 | 5/2009 | Altshuler et al. |
| 2009/0281433 | A1 | 11/2009 | Saadat et al. |
| 2010/0081957 | A1 | 4/2010 | Hyde et al. |
| 2011/0053173 | A1 | 3/2011 | Hood et al. |
| 2012/0009539 | A1 | 1/2012 | Goodson et al. |
| 2012/0021375 | A1 | 1/2012 | Binner et al. |
| 2012/0123225 | A1 | 5/2012 | Al-Tawil |
| 2012/0165694 | A1 | 6/2012 | Meka et al. |
| 2012/0172677 | A1 | 7/2012 | Logan et al. |
| 2012/0172678 | A1 | 7/2012 | Logan et al. |
| 2012/0172679 | A1 | 7/2012 | Logan et al. |
| 2012/0207806 | A1 | 8/2012 | LoPesio |

OTHER PUBLICATIONS

"Toothpastes" by L. Rigano. Cosmetics & Toiletries vol. 127 pp. 324-332. 2012.*

"What is in Toothpaste? Five Ingredients and what they do" by A. Freeman at Colgate. Accessed at: http://www.colgate.com/en/us/oc/oral-health/basics/selecting-dental-products/article/what-is-in-toothpaste-five-ingredients-and-what-they-do-0814. Wayback machine date Jun. 20, 2016.*

* cited by examiner

CLOSED SYSTEM MOUTHPIECE WITH LIGHT AND HEAT GENERATION TO ACTIVATE A FORMULATION TO INCREASE ITS VOLUME

This application is a continuation-in-part of application Ser. No. 13/956,787, filed Aug. 1, 2013.

BACKGROUND OF THE INVENTION

The present invention relates to a closed system mouthpiece with light and heat generation to activate a formulation to increase its volume.

Most natural environments harbor an incredibly diverse collection of microbial species. Within these communities, bacteria compete with their neighbors for space and resources.

The mouth is no different, with a warm, nutrient rich environment, continuously bathed with saliva, and with a pH normally between 6.75-7.25, essentially neutral between acidic and basic. The oral cavity is a home for around 600 species and 8 billion bacteria all living together and vying for nutrients and resources to feed themselves, most of which are beneficial organisms and live in harmony with each other and the host.

How do all of these bacteria in one's mouth live together over time to maintain this natural healthy balance between good bacteria and the bad bacteria. Survival is key and the natural selection theory holds true over time. The microbiological community figures out how to live together, and not only survive, but to thrive in this natural ecosystem. The ability to work together and share the resources in their community is referred to as homeostasis, a balancing act that lives in our mouth in spite of numerous external changes.

However, when the external changes are too powerful for the homeostatic balance, the bacterial balance in the mouth shifts significantly. The bacteria that can cause harm begin to dominate the beneficial organisms. That is, shifts in the environment can throw the balance off between bacteria that have a positive effect vs. bacteria that cause disease. The three main environmental shifts are the pH of the mouth (acid and base balance), the availability of nutrients (food and resources) in our mouths, and how well we are cleaning the plaque off our teeth and gums; especially in the hard to reach places.

It is not the individual bacteria alone that cause disease, but the environment in our mouth that is altered by our diet and our ability to control plaque, both events we control by our daily actions. These actions directly affect the environmental circumstances in regulating and controlling the quality of the biofilm (bacterial plaque) in our mouths, the types of nutrients we put into our mouths, and the resulting pH.

For people who have a diet high in proteins (i.e., meat, processed foods) and simple carbohydrates or sugars, a low pH unhealthy, acidic environment is formed. This helps the acid tolerating bacteria like *s. mutans* that cause disease and displaces the oral-health associated, neutral pH bacteria such as *s. salivarius*. Another example of this phenomenon is the gram-negative anaerobic bacteria that also thrive in the more acidic environment that causes an inflammatory cascade to occur in the periodontal tissues and resulting gingivitis. Similarly, the bad breath causing bacteria that live in between the teeth and in the deep surfaces of the tongue also thrive in the acidic environment that decreases saliva flow and increases colonization of the harmful bacteria. So, by having a lower pH in our mouths because of what we put in our mouths and due to our food selection, the bacteria that cause decay, gum disease and bad breath start dominating the healthy bacteria. Couple this with poor plaque control, and the environment is now created for a shift in the bacterial populations to disease producing organisms and a bacterial load that not only impacts oral health, but overall health as well.

Today, the link between pathogenic bacteria originating in the oral cavity causing inflammation in other areas of the body has been scientifically demonstrated.

Dr. Han and her co-investigators have begun identifying the mechanisms that allow *F. nucleatum* to move from the mouth into the bloodstream and throughout the body—taking other bacteria with it and leaving destruction in their path (*Molecular Microbiology*, December 2011, Vol. 82:6, pp. 1468-1480). Her team has shown that *F. nucleatum* can induce preterm birth and stillbirth in animals and humans (see, for example, *Obstetrics & Gynecology*, February 2010, Vol. 115: suppl 2, part 2, pp. 442-445). Other researchers have linked this phenomenon to colorectal cancer (*Genome Research*, Oct. 18, 2011) and infections and abscesses in all the internal organs, including in the brain and lungs.

By controlling pH to maintain it within desirable limits, it is possible to alter the plaque biofilm, remineralize existing lesions and help prevent oral disease going forward.

Plaque is a very sticky substance that forms on the teeth in a matter of minutes and causes gum inflammation in a matter of days if the plaque is not timely removed. The areas in the mouth that are difficult to clean are the surfaces of the tongue and areas between the teeth that create an anaerobic environment. Without oxygen, the bacteria that cause bad breath and periodontal disease now colonize if they are not timely removed. If we look at ways to mitigate the dominance of the bad bacteria over the healthy ones, if we can impact the pH of our mouths and effectively decrease the bad bacteria in the mouth, we will have an effective way to promote good health in the mouth. The objective is to change the environment from oxygen poor-low pH sites where the pathogenic bacteria thrive to a safer, more effective way to rebalance homeostasis in the mouth toward enhanced health with an oxygen-rich-higher ph.

We know that only 10% of the population flosses regularly and that 75% of the population over the age of 35 has some form of gum disease. The latest data from the NIH and the Academy of Periodontics is that half the adult population has some form of periodontal disease, which is gum inflammation along with bone loss. These chronic type lesions are the ones that show an increase in bacterial load in the mouth which impacts areas all over the body as the oral disease bacteria have the chance to be disseminated to other areas in the body. The connection between oral health and overall health is an emerging science of oral systemic medicine and has been growing over the last decade. Moise Desvarieux, an infectious disease epidemiologist at Columbia University, conducted studies showing the link between chronic infections, including periodontal infections, and cardiovascular disease. Dr. Angela Kamer, Assistant Professor of Periodontology & Implant Dentistry at New York University, led a research team that found a connection between periodontal disease and cognitive function, citing higher levels of antibodies and inflammatory molecules associated with periodontal disease in Alzheimer's patients over healthy people. The British Medical Journal posted a study conducted by researchers at Brown University stating that individuals with high levels of *Porphyromonas gingivalis* bacterium had twice as great a risk of developing pancreatic cancer over individuals with lower levels of these bacterium.

Oral care products traditionally have focused on taking either a specific kill of a bacterium or to indiscriminately kill all bacteria. This thinking needs to be replaced with an approach that improves the environment to change the bacterial balance in the mouth in a safe way that will have a healthier and more balanced affect long term.

The use of light and heat in oral care is known to kill bacteria in the 470-490 nm wavelength range. The use of light alone will have an impact specifically on $p.$ $gingivalis$ and to eliminate this bacteria.

We also know that the light and antibacterial approaches attacking the organisms will only have a short term effect.

What has not been used in the past is a mouthpiece with light and heat built inside, that creates a sealed gasket effect for any formulation that will be placed inside of it. It would be advantageous to couple a mouthpiece with a formulation that changes a gel to foam when warmed along with the mouthpiece that has light and heat installed therein. A universally shaped mouthpiece allows for a custom fit as its internal flex circuit shapes to the user's mouth when they bite down on its platform area.

It would be advantageous for the light and heat of a mouthpiece to activate a formulation to transform it from a gel to foam. Such a foam increases in volume and as contained in the closed system mouthpiece drives its active ingredients to the very difficult areas that require meticulous plaque control. These areas between the teeth, furthest areas back in the mouth and on the tongue, need this level of diligence.

In the prior art, post foaming agents are generally known which convert gel-like compositions to foam through application of heat. Post foaming agents are found in many personal care and over the counter products such as shampoos, conditioners, and activated skin treatments. When a post foaming gel is exposed to the combination of heat and light, the foaming agent is volatilized. During this process, thousands of tiny gas bubbles are created and interact with surfactants. A foaming rinse is typically created that delivers active ingredients of a formula incorporated into the post foaming gel to provide desired benefits.

Post foaming products known to Applicants utilize a blend of isopentane ($C_5H_{12}$) with a boiling point of 27.7° C. and isobutane ($C_4H_{10}$) with a boiling point of –11.7° C. as the foaming agent. The ratio of this blend can vary but it generally is 65% isopentane and 35% isobutane. The percentage of foaming agent in a product typically varies from 2% to 5%, or sometimes more depending upon the amount of foaming desired.

Applicants conducted laboratory and patient trials in which a foaming agent consisting of the combination of isopentane and isobutane was included in a proportion of 1% to 6%. These trials varied the percentage in one percent increments. Additionally, these trials varied the proportions of the constituent ingredients of the foaming agent so that the proportion of isopentane was varied from 50% to 85% in 5% increments.

Applicants analyzed the results of these laboratory and patient trials and concluded that none of the blends of foaming agent performed satisfactorily because, in each case, foaming occurred too quickly (at an unacceptably low temperature) and not consistently throughout application and use of the product. In this regard, the most advantageous scenario is for the post foaming gel to begin to foam only after it has been inserted into the oral cavity. These experimental products typically began to foam prior to insertion into the oral cavity.

Upon careful analysis, Applicants concluded that the reason the post foaming gel began to foam prior to insertion into the oral cavity was the presence of isobutane with its low boiling point (–11.7° C.). Accordingly, in formulating the inventive post foaming gel, isobutane was eliminated from the mixture and the post foaming agent comprises solely isopentane. Upon further experimentation, Applicants found that employing a post foaming agent solely comprising isopentane resulted in foaming action occurring only subsequent to insertion into the oral cavity.

People have always had trouble routinely brushing and flossing which keeps the bacteria in a healthy balance of good vs. bad bacteria. Once the plaque is allowed to form on the teeth close to the gums, over the course of just a few days, the bacterial microflora change to the more pathogenic anaerobes that cause disease. The oral care regimen needs to be easy to use, short in duration, healthy and safe long term, and must fit into people's lifestyles. In the past, minutes of brushing and 2 minutes to floss has not seen great success because of the technique sensitivity (user's ability) and the amount of time required to fit into people's busy lifestyles.

Applicants' original invention involves incorporation of light and heat to optimize the effectiveness of a whitening formulation by keeping the actives around longer and pushing them into the hard to reach areas to whiten. This mouthpiece has a warming element with a TPR or other thermoplastic material that warms, softens, and conforms to the mouth upon use to create a peripheral seal around the outside of the mouthpiece to seal actives inside. The universal mouthpiece, because of the flexible circuits, fits to any mouth, any arch form and the thermoplastic material forms the peripheral seal closed system.

The mouth is a dark, moist environment, where the hard to reach areas are void of oxygen, creating the perfect living headquarters for the anaerobic bacteria that thrive and cause the most damage.

It is known in the prior art to measure the level of acidity or basic characteristic within a person's mouth. However, Applicants are unaware of any prior art teaching measuring of the pH in the mouth of a user in the manner contemplated in the present invention. Applicants are aware of the following prior art:

| U.S. Published Patent Applications | |
|---|---|
| 2005/0113654 to Weber et al. | 2011/0053173 to Hood et al. |
| 2008/0233541 to De Vreese et al. | 2012/0123225 to Al-Tawil |
| 2009/0017422 to Creamer | 2012/0165694 to Meka et al. |
| 2009/0132011 to Altshuler et al. | 2012/0172677 to Logan et al. |
| 2009/0281433 to Saadat et al. | 2012/0172678 to Logan et al. |
| 2010/0081957 to Hyde et al. | 2012/0172679 to Logan et al. |
| U.S. Patents | |
| 5,674,182 to Suzuki et al. | 6,607,387 to Mault. |

While each of these references teaches some aspect of sensing pH, none of them teaches the manner of doing so contemplated in the present invention.

Generally speaking, it is known in the prior art to utilize light at desired wavelengths to kill orally located germs. Applicants are aware of the following prior art references:

| U.S. Published Patent Applications | |
| --- | --- |
| 2004/0010299 to Tolkoff et al. | 2012/0021375 to Binner et al. |
| 2008/0032252 to Hayman et al. | 2012/0207806 to LoPesio. |
| 2012/0009539 to Goodson et al. | |
| U.S. Patents | |
| 7,223,270 to Altshuler et al. | 7,329,274 to Altshuler et al. |
| 7,223,281 to Altshuler et al. | 7,354,448 to Altshuler et al. |
| 7,329,273 to Altshuler et al. | 7,422,598 to Altshuler et al. |

The prior art references listed above generally disclose the use of light to kill bacteria, the use of light intra-orally, the use of the combination of mouthpieces and solutions to kill mouth bacteria, and the use of light in a toothbrush for oral phototherapy. Hayman et al. disclose use of a mouthpiece and use of light to kill bacteria.

While these references teach the concept of using light to kill bacteria in the mouth, in a general sense, none of these references taken alone or in combination with other references teaches or suggests the specific manner by which the present invention employs a mouthpiece, heat and light, and a foaming substance within a hermetically sealed environment to retain or restore an advantageous pH level within the mouth of a user to maintain oral health and general health.

SUMMARY OF THE INVENTION

The present invention relates to a formulation that starts as a gel and transforms into a foam under influence of light and heat to expand out into the oral cavity of a user for advantageous health benefits. The present invention employs a closed system mouthpiece with light and heat generation to activate the formulation to increase its volume. The present invention includes the following interrelated objects, aspects and features:

(1) The present invention employs a gel formulation that may be coated into a mouthpiece, the mouthpiece subsequently being inserted into the mouth of the user.

(2) Application of heat above a threshold temperature causes the gel to transform into foam and expand out of the mouthpiece and into the oral cavity.

(3) The mouthpiece is specifically designed to create a hermetic seal such that the mouth behind the teeth is transformed into a sealed chamber. Thus, when the application of heat causes the gel to expand into foam, the foam expands out throughout the oral cavity into nooks and crannies that are normally difficult to access.

(4) With the foam so dispersed within the oral cavity, activation of a light source embedded within the mouthpiece enhances the bacteria killing properties of the now foam material. This sealing property of the mouthpiece is described by Applicants as a "gasket effect."

(5) The foam spreads onto the tongue of the user as well and acts to kill any damaging bacteria found there. As a result of operation of the present invention, the pH balance of the mouth is restored to a neutral level in the range of 6.75 to 7.25 or maintained at that pH level in which a healthy balance is maintained between various species of bacteria. With damaging bacteria killed through use of the mouthpiece and the gel transforming into foam, the pipeline feeding damaging bacteria throughout the body is cut off, thereby enhancing overall health of the user.

(6) The formulation includes as the post foaming agent isopentane. To achieve the objects of the present invention, the formulation also includes as essential ingredients Sorbitol, hydrogen peroxide, PVP K90, silicon dioxide, PEG, Xylitol, sodium bicarbonate, tetrasodium EDTA, and CPC, and the balance water.

(7) Optional ingredients include propylene glycol, Wintermint, Poloxamer 188, potassium olivoyl hydrolyzed oat protein surfactant, Magnasweet, Ammonium Glycyrrhizate, Dimethyl Isosorbide, Sodium Silicate Pentahydrate, menthol, BHT, vitamin E, and sodium hydroxide. The purposes for these optional ingredients will be described in greater detail hereinafter.

As such, it is a first object of the present invention to provide a formulation that transforms from gel to foam upon exposure to heat and light to provide a user health-related advantages.

It is a further object of the present invention to employ the inventive formulation in conjunction with a mouthpiece with integral light and heat sources to facilitate illuminating and heating the inside of the mouth of a user.

It is a still further object of the present invention to provide such a device in which a gel may be coated, which gel expands into foam when exposed to heat above a threshold temperature.

It is a still further object of the present invention to provide such a mouthpiece including structure to create a hermetic seal about the teeth and gums of the user to seal the oral cavity from outside the mouth to fulfill the purposes of the present invention. The structure of the gasket effect of the mouthpiece includes a peripheral flange that creates a "gasket flange" that has a wiper blade and a rolled peripheral seal to ensure a tight seal to create a sealed environment.

It is a yet further object of the present invention to provide such a system in which the foam expands throughout the oral cavity to kill anaerobic bacteria (bacteria that live without oxygen) in the hard to reach places and restore the pH of the mouth to within a healthy range.

It is a yet further object of the present invention to activate a source of light within the mouthpiece to perform additional therapeutic functions.

It is a yet further object of the present invention to provide such a mouthpiece in which a pH sensor is integrally mounted to facilitate close monitoring of the pH of the mouth to fulfill the therapeutic purposes of the present invention. The pH sensor will tell the wearer when their mouth is healthy, and using specific formulations will improve the overall health through pH detection.

These and other objects, aspects and features of the present invention will be better understood from the following detailed description of the preferred embodiments when read in conjunction with the appended drawing figures.

SPECIFIC DESCRIPTION OF THE PREFERRED EMBODIMENT

Figure 1:
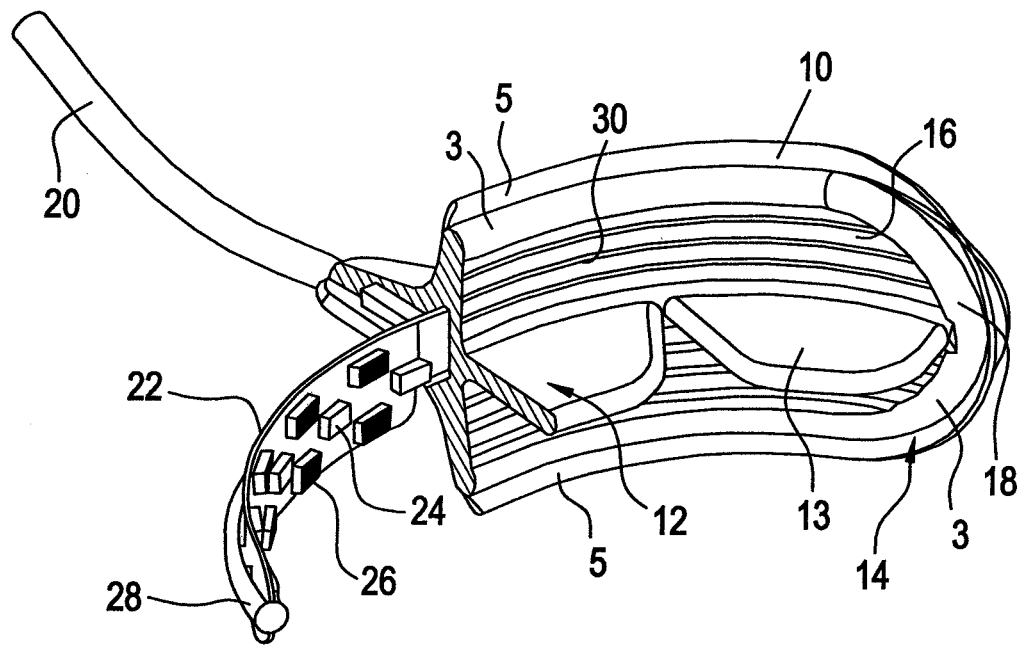
FIG. 1 shows a perspective view of the inventive mouthpiece with portions broken away to show details of the embedded flexible circuit.
Figure 2:
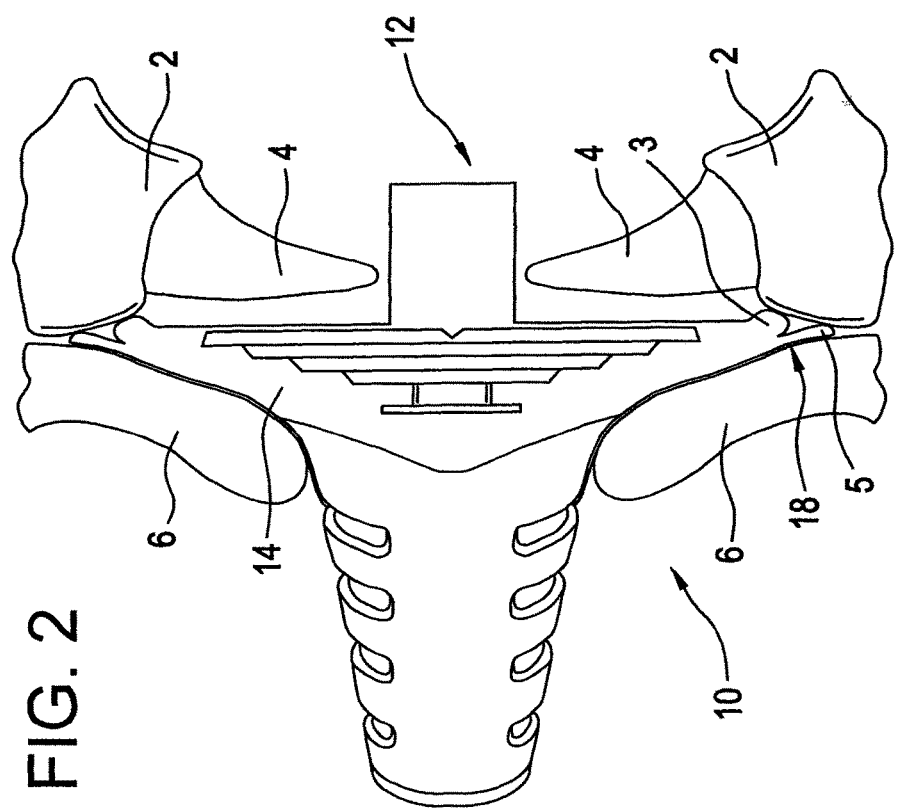
FIG. 2 shows a cross-sectional view which depicts how the flexible circuit is located embedded within the mouthpiece and the mouthpiece effects a hermetic seal of the oral cavity.

In order to best understand how the inventive formulation is employed by a user, it is instructive to first explain in detail the details of the delivery system which consists of the inventive mouthpiece, in conjunction with the accompanying drawing figures. Thus, with reference first to FIGS. 1 and 2, the inventive mouthpiece is generally designated by the reference numeral 10 and includes a bite surface 12, central and perpendicular to the main body 14, and which extends outwardly from a central portion of the inner surface of the main body on one side thereof as best seen in FIG. 2. The bite surface 12 is configured to ensure stability of the mouthpiece 10 when it is positioned in the user's mouth between the upper and lower arches. The bite surface 12 may be formed from two or more segmented or separated portions, or, alternatively can be made of a single continuous bite surface 13. The segmented bite surface is preferred because it better allows for adjustments in the curvature of the mouthpiece 10 to more easily adapt to mouths of differing shapes and configurations. The mouthpiece includes a double seal bead 18 (FIGS. 1 and 2) extending about its periphery that is designed to seal at just above the gum margins to provide a hermetic sealed environment within the oral cavity when the mouthpiece is in place. The double seal bead includes a seal bead 3 and a wiper blade 5. These seals extend about the periphery of the mouthpiece 10 and seal at the margin of the gums 2, thereby creating a closed chamber in the oral cavity, isolating the teeth 4 from the atmosphere. The lips 6 of the user lie over the body of the mouthpiece as seen in FIG. 2 to further enhance sealing effect. A plurality of textured bands 16 (FIG. 1) are also provided, specifically designed to channel LED light more diversely over the entirety of the teeth and oral cavity. The bite surface 12 is specifically designed to be transparent so that light from the LEDs embedded within the mouthpiece (as will be described in greater detail hereinafter) and co-planar with the bite surface 12 can find its way behind the teeth and into the oral cavity for purposes to be described in greater detail hereinafter. As explained above, reflective surfaces within the mouthpiece enhance light transmission and its spread within the oral cavity. Reflective surfaces are also provided in the mouthpiece to guide light from the LEDs 24 into the oral cavity. (Jonathan, please provide the structure of the reflective surfaces.)

Embedded within the mouthpiece 10 is a flexible circuit board 22 that has integrally mounted therein two rows of heat generating resistors 26 between which is a single row of illuminating LEDs 24. The flexibility of the circuit board 22 permits the mouthpiece 10 to be bent to adapt to differing curvatures and configurations of differing user mouths. In the preferred embodiment of the present invention, the inner surface 30 of the mouthpiece above and below the bite surface 12 is tilted inward at an angle in the range of 5 to about 15 degrees to enhance the seal of the peripheral bead 18. This is seen with particular reference to FIG. 2 which shows, schematically, a tooth 34 as well as the gum 35 with the seal bead 18 sealing at the margin between the tooth 34 and the gum 35 so that beams of light 32 impinge upon all of the tooth surfaces, in use. Reference numeral 20 depicts an electrical conductor which supplies power to the flexible circuit board 22 from a source of power not shown in FIGS. 1 and 2. Many of the details described above are also found in Applicants' prior U.S. Pat. No. 8,371,853, the details of which are incorporated by reference herein.

The inventive mouthpiece disclosed in U.S. Pat. No. 8,371,853 was disclosed as principally usable for teeth whitening. It was also disclosed as usable in methods of desensitizing teeth, accelerating healing of mouth sores or ulcerations, for treating gum disease or freshening a patient's breath. The present invention expands upon the uses contemplated in Applicants' prior mouthpiece invention by operating in conjunction with a formulation usable for other purposes.

In particular, the present invention is intended to be used in connection with a gel formulation which when heated above a threshold temperature transforms into foam dramatically expanding its volume and spreading throughout the oral cavity for the purposes disclosed herein. Such a gel may include as constituent ingredients including PEG-8, propylene glycol, canola oil, hydrogen peroxide, glycerin, dimethylisosorbide, a formulation of poloxamer ascorbic acid, xylitol, and other substances including flavoring and coloration. In essence, the substance employed may be spread over the surfaces of the mouthpiece and maintains its gel consistency at room temperature. However, when placed in the mouth, the mouth temperature begins to raise the temperature of the gel. When the heating resistors 26 are activated, they elevate the temperature of the mouth over 100° F. At the designed temperature threshold, the gel begins to expand, transforming into foam that begins to spread throughout the oral cavity coating all of the tooth surfaces as well as the surfaces of the oral cavity including the tongue, the roof of the mouth, interstices between teeth and gums, and other hard to reach areas. In the preferred embodiment, the gel begins to slowly transform into foam at the normal temperature of the oral cavity, 37° C. With the heating resistors 26 activated, at 40° C., the transformation speeds up. The heating resistors 26 can heat the oral cavity to up to about 50° C., a high enough temperature to quickly transform the gel into foam without making the user uncomfortable from the heat.

The premise for the formulation of the post foaming gel of the present invention is that it contains antimicrobial agents in a high pH environment killing germs that result, for example, in the creation of plaque and the development of periodontal disease. Antimicrobial agents can be Cetylpyridinium Chloride (CPC) and Hydrogen Peroxide ($H_2O_2$). Throughout formula development, the concentrations of each of these antimicrobial agents has varied from 0.05%-1.00% and 1.0%-3.0% for CPC and $H_2O_2$, respectively. Higher concentrations of these antimicrobial agents were found not always to improve the effectiveness of the product as significant-pH-changes were observed (lowering) which negatively impacted their effectiveness, especially with $H_2O_2$. To obtain optimum performance from these antimicrobial agents, Applicants found that the sustained pH of the product must remain at or above 7.5. The inventive formula also contains Sodium Bicarbonate ($NaHCO_3$) at levels between 0.1%-1.0% which help deodorize the mouth and is primarily responsible for the "clean mouth feel." $NaHCO_3$ and $H_2O_2$ do not normally coexist in a formula as their tendency is to react and neutralize each other.

Maintaining the balance of these ingredients at a pH level where they would be effective ($\geq 7.5$) required a holistic evaluation of the formulation where:

(a) Ingredients that promote disassociation of $H_2O_2$ and the subsequent lowering of pH and neutralization of $NaHCO_3$ would be minimized or eliminated from the formula;

(b) Ingredients that promoted the coexistence of $H_2O_2$ and $NaHCO_3$ and stabilized pH would be added or increased in the formula.

Throughout development of the inventive formulation, many variations were evaluated and some of the more significant changes that support the points above are as follows:

(a) Glycerin concentrations ranged from 10%-40% in formula variants and were finally eliminated from the formula due to its aggressiveness toward $H_2O_2$;

(b) Sorbitol concentrations ranged from 10%-50% in formula variants as the "sweetness" and ability to incorporate isopentane were balanced;

(c) Peroxydone K-90 was replaced with Peroxydone XL-10 (plasdone hydrogen peroxide complex) which proved to be a more stable form of $H_2O_2$ of higher concentration;

(d) Carbowax 3350 was replaced with Polyethylene Glycol 300 due to its greater compatibility with $H_2O_2$;

(e) Sodium Silicate Pentahydrate was added to the formula and tested with ranges of 0.05%-0.25% due to its ability to assist in the stability of $H_2O_2$ and subsequent pH stability;

(f) Tetrasodium EDTA was added to the formula and tested in ranges between 0.05%-0.25% due to its ability to chelate metal ions and stabilize $H_2O_2$;

(g) Butylated Hydroxytoluene (BHT) was added to the formula and tested in ranges between 0.05%-0.20% due to its anti-oxidant preservative nature.

The inventive formulations had many iterations in the course of its finalization wherein the stability of the antimicrobial agents in an alkaline pH was preserved.

In the preferred embodiment of the present invention, the formulation includes the constituent ingredients as set forth in Table 1 below. Of the constituent ingredients listed, some are mandatory and others are optional in that the general category of ingredient is included but the specific example may differ. Table 2 below provides more details. Applicants note that the "Range Percent" refers to the percent of the percentage. Thus, for example, Isopentane is provided in 3%±2%. This means a range of 2.94% to 3.06%. Also, the listed percentages are by weight. Table 3 lists the ingredients, stating which are mandatory as to the specific name and which are optional as explained above.

TABLE 1

ECO Balance Formulation

| Ingredient Trade Name | Target Percent | Range Percent | Function |
|---|---|---|---|
| RO/DI Water | 33.163% | +/−2.00% | Solvent |
| Sorbitol Solution (70%) | 19.413% | +/−2.00% | Sweetening agent—humectant |
| Propylene Glycol* | 15.478% | +/−2.00% | Penetration enhancer—humectant |
| plasdone hydrogen peroxide complex | 7.275% | +/−2.00% | Antimicrobial agent—whitening |
| PVP K90 | 5.332% | +/−2.00% | Thickening agent |
| Aerosil 200 (Evonik) | 4.850% | +/−2.00% | Thickening agent |
| PEG 300 | 4.850% | +/−2.00% | Emulsifier |
| Isopentane | 3.000% | +/−2.00% | Post foaming agent |
| Intensates Glowing Wintermint TAK-130158* | 1.358% | +/−2.00% | Flavor |
| Xylitol | 1.261% | +/−2.00% | Sweetening agent—humectant |
| Pluracare F-68 (Poloxamer 188)* | 0.970% | +/−2.00% | Surfactant—cleansing agent |
| potassium olivoyl hydrolyzed oat protein | 0.970% | +/−2.00% | Surfactant—emolient |
| Magnasweet 110 F* | 0.534% | +/−2.00% | Flavoring agent |
| Arasolve DMI-PC-LQ* | 0.485% | +/−2.00% | Penetration enhancer—humectant |
| Sodium Bicarbonate | 0.291% | +/−2.00% | pH raiser—deodorizer |
| Sodium Silicate Pentahydrate* | 0.194% | +/−2.00% | pH stabilizer |
| Tetrasoclium EDTA | 0.146% | +/−2.00% | Chelating agent |
| Menthol* | 0.110% | +/−2.00% | Flavoring agent |
| Butylated Hydroxytoluene (BHT)* | 0.097% | +/−2.00% | Preservative |
| Cetylpyridinium Chloride (CPC) | 0.097% | +/−2.00% | Antimicrobial agent |
| Vitamin E Acetate (Tocopheryl Acetate)* | 0.097% | +/−2.00% | Antioxidant |
| Sodium Hydroxide (100%)* | 0.029% | +/−2.00% | pH raiser |

Optional ingredients denoted by "*"

TABLE 2

| Ingredient Trade Name | INCI Name | Target Percent | Range Percent | Function |
|---|---|---|---|---|
| RO/DI Water | Aqua (Water) | 33.163% | +/−2.00% | Solvent |
| Sorbitol Solution (70%) | Sorbitol | 19.413% | +/−2.00% | Sweetening agent—humectant |
| Propylene Glycol* | Propylene Glycol | 15.478% | +/−2.00% | Penetration enhancer—humectant |
| plasdone hydrogen peroxide complex | PVP Hydrogen Peroxide | 7.275% | +/−2.00% | Antimicrobial agent—whitening |
| PVP K90 | Polyvinylpyrrodidone K 90 | 5.332% | +/−2.00% | Thickening agent |
| silicon dioxide | Silicon Dioxide | 4.850% | +/−2.00% | Thickening agent |
| PEG 300 | Polyethylene glycol 300 | 4.850% | +/−2.00% | Emulsifier |

TABLE 2-continued

| Ingredient Trade Name | INCI Name | Target Percent | Range Percent | Function |
|---|---|---|---|---|
| Isopentane | Isopentane | 3.000% | +/−2.00% | Post foaming agent |
| Intensates Glowing Wintermint TAK-130158* | Flavor | 1.358% | +/−2.00% | Flavor * |
| Xylitol | Xylitol | 1.261% | +/−2.00% | Sweetening agent—humectant |
| Pluracare F-68 (Poloxamer 188)* | Poloxamer 188 | 0.970% | +/−2.00% | Surfactant—cleansing agent |
| potassium olivoyl hydrolyzed oat protein | Potassium Olivoyl Hydrolyzed Oat Protein, cetearyl alcohol, glyceryl stearate | 0.970% | +/−2.00% | Surfactant—emolient |
| Magnasweet 110 F* | Ammonium Glycyrrhizate | 0.534% | +/−2.00% | Flavoring agent |
| dimethyl isosorbide | Dimethyl Isosorbide | 0.485% | +/−2.00% | Penetration enhancer—humectant |
| Sodium Bicarbonate | Sodium Bicarbonate | 0.291% | +/−2.00% | pH raiser—deodorizer |
| Sodium Silicate Pentahydrate* | Sodium Metasilicate Pentrahydrate | 0.194% | +/−2.00% | pH stabilizer |
| Tetrasodium EDTA | Ethylenediaminetetraacetic acid | 0.146% | +/−2.00% | Chelating agent |
| Menthol* | Menthol | 0.110% | +/−2.00% | Flavoring agent |
| Butylated Hydroxytoluene (BHT)* | Butylated hydroxytoluene | 0.097% | +/−2.00% | Preservative |
| Cetylpyridinium Chloride (CPC) | Cetylpyridinium Chloride | 0.097% | +/−2.00% | Antimicrobial agent |
| Vitamin E Acetate (Tocopheryl Acetate) | Tocopheryl Acetate | 0.097% | +/−2.00% | Antioxidant |
| Sodium Hydroxide (100%)* | Sodium Hydroxide | 0.029% | +/−2.00% | pH raiser |

Optional Ingredients denoted by "*"

TABLE 3

Figure 3:
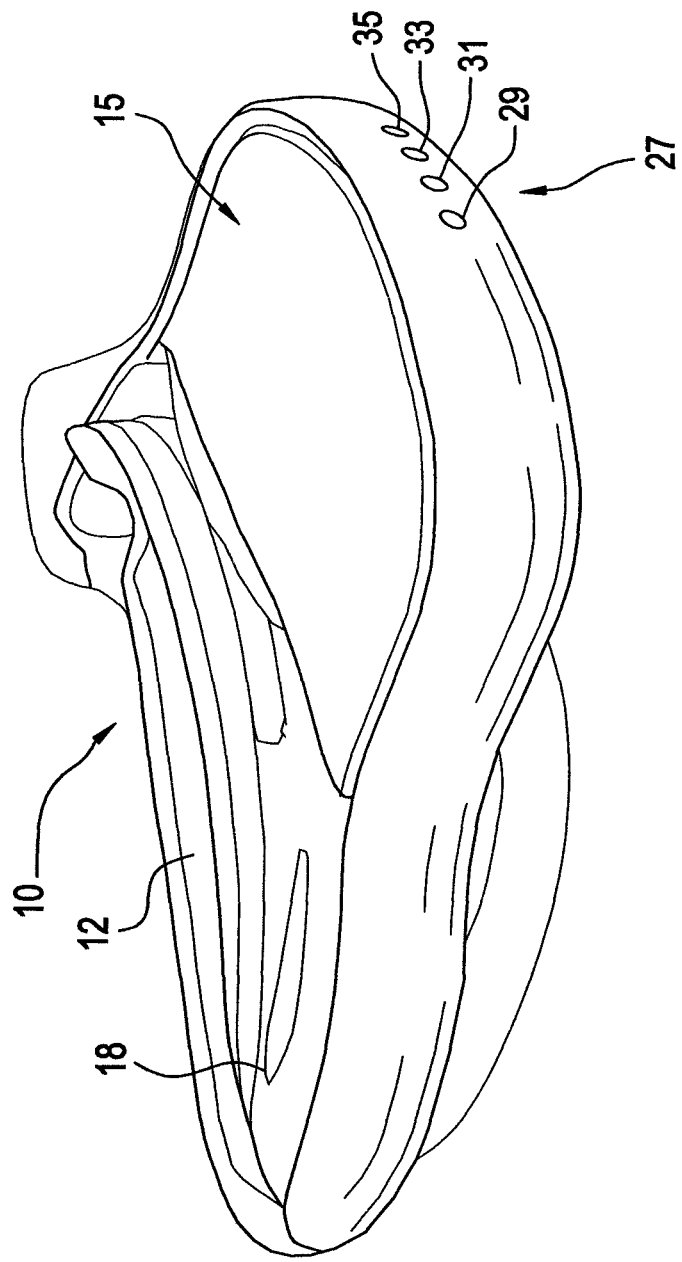
FIG. 3 shows a further perspective view of the inventive mouthpiece showing further details including those of aspects of its pH sensor.
Figure 4:
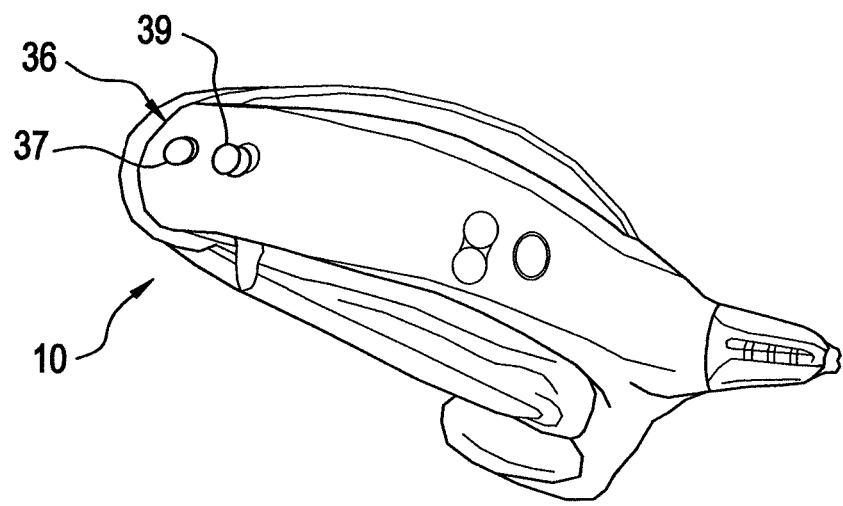
FIG. 4 shows a side view of the inventive mouthpiece showing the electrodes of the pH sensor.
Figure 5A:
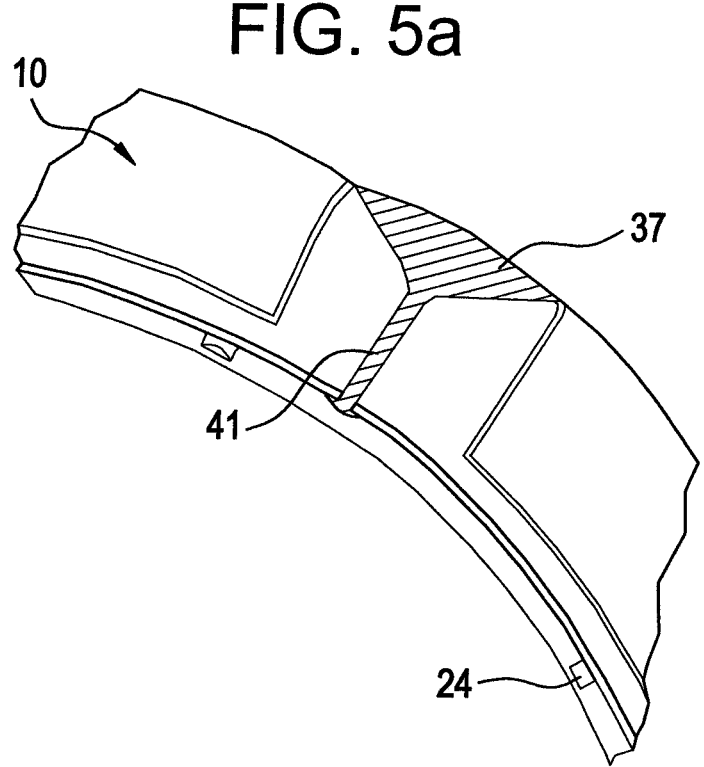
FIG. 5a shows a schematic representation of some of the circuitry of the inventive mouthpiece.

Ingredients:

Water --> essential
Sorbitol --> essential
Propylene glycol --> optional
PVP Hydrogen peroxide --> essential
PVP K90 --> essential
Silicon dioxide (Aerosil 200) --> essential
PEG --> essential
Isopentane --> essential
Wintermint --> optional
Xylitol --> essential
Poloxamer 188 --> optional
Olivoyl Avenate (potassium olivoyl hydrolyzed oat protein) surfactant --> optional
Magnasweet --> optional
Ammonium glycyrrhizate --> optional
Dimethyl Isosorbide --> optional
Sodium Bicarbonate --> essential
Sodium Silicate Pentahydrate --> optional
Tetrasodium EDTA --> essential
Menthol --> optional
BHT --> optional
CPC --> essential
Vitamin E --> optional
Sodium hydroxide --> optional With reference to FIGS. 3, 4 and 5a, the mouthpiece 10 has a gripping tab 15 that may be gripped by the user in placing the mouthpiece 10 within the oral cavity. The gripping tab 15 also includes a display 27 that includes a series of lights 29, 31, 33 and 35. Those lights comprise a display used in conjunction with a pH sensor incorporated into the inventive device. With reference to FIG. 4, the electrodes 37 and 39 are located on the mouthpiece 10 in a location in which they are consistently immersed in saliva. The saliva between the electrodes 37 and 39 closes an electrical circuit that may be measured as a voltage that corresponds to the pH of the oral cavity. FIG. 5a shows the electrode 37 embedded within the mouthpiece 10 and including a conductor 41 preferably made of a material such as copper.

In more detail, the pH sensor electrodes 37 and 39 are made of a pH sensitive material and are electrically connected to the flexible circuit board 22. The preferred location for the electrodes is at either end of the arch of the mouthpiece 10. The electrodes may be made of any solid material that develops hydrogen ion dependent electrical potentials. Such materials include Iridium Oxide, Silver Chloride, Graphene, Carbon Nanotubes, and other Nano materials.

As the electrodes are exposed to saliva, they develop a measurable electrical potential. The electrical potential on the electrodes is measured as a voltage and correspondingly increases or decreases responsive to the pH value of the saliva. The voltage measured at the sensor is computed by a microprocessor in the mouthpiece and converted into an indication of the pH. The measured pH is displayed by the color coded lights 29, 31, 33 and 35 of the display 27, in one embodiment thereof. In one embodiment of color-coded indicator lights, a green indicator light can be used to signify a pH of saliva within a healthy range, for example, 6.75 to 7.25. A red indicator light can be used to signify a pH of saliva in an unhealthy range, for example, below 6.75. In another variation, the red and green lights can be programmed to illuminate responsive to other pH ranges. Thus, the green light can be illuminated to signify a healthy pH for saliva where the pH is 7.0 or higher, and the red light can be illuminated to signify a saliva pH of below 7.0. In another embodiment, the display can be separate from the mouthpiece and the microprocessor can be connected to the display via a remote wired or wireless link. In either embodiment, a preferred manner of practicing the present invention is to measure the pH of saliva in the user's oral cavity before the mouthpiece is coated with gel and before the LEDs and heating resistors are activated. In this way, the baseline measurement of pH before treatment can be established so that restoration of the pH to a healthy range can be demonstrated. As is well known by those of ordinary skill in the art, pH below 7.0 signifies acidic saliva which demonstrates the existence of active disease. Through practice of the present invention, the pH of saliva in the oral cavity is elevated to a neutral pH signifying a healthy oral cavity.

In more detail, it is well known by those of ordinary skill in the art that the pH of a liquid can be measured by employing two spaced electrodes. As explained in *WHAT IS pH, AND HOW IS IT MEASURED? A Technical Handbook for Industry*, by Frederick J. Kohlmann, © 2003 Hach Company (which is incorporated by reference herein), in the $19^{th}$ century, Hermann Walther Nernst introduced the Nernst equation which resulted in definition of the Nernst factor which provides the amount of change in total potential for every ten-fold change in ion concentration. In essence, Nernst determined that for every pH unit change, the total electrical potential will change by 59.16 mV.

With this information in mind, Kohlmann describes the use of a pair of electrodes, one of which is a reference electrode, and the other of which is a measuring electrode. When the measured potential between these two electrodes is zero, this equates to a pH measurement of 7.0, neutral pH. As the solution becomes more acidic (a pH below 7), the mV potential becomes more negative at a rate of 59.16 mVs for every unit reduction in the pH value. Thus, a voltage reading of −59.16 mVs equates to a pH of 6.0. Conversely, as the solution becomes more basic (a pH above 7), the mV potential becomes more positive at a rate of 59.16 mVs for every unit increase in the pH value. Thus, a voltage reading of +59.16 mVs equates to a pH of 8.0. With this information in hand, it is easy to see how one of ordinary skill in the art can devise a display, whether analog, digital, or employing indicator lights, to indicate to the user the pH of saliva within the oral cavity of the user, which saliva immerses the spaced electrodes.

Figure 5B:
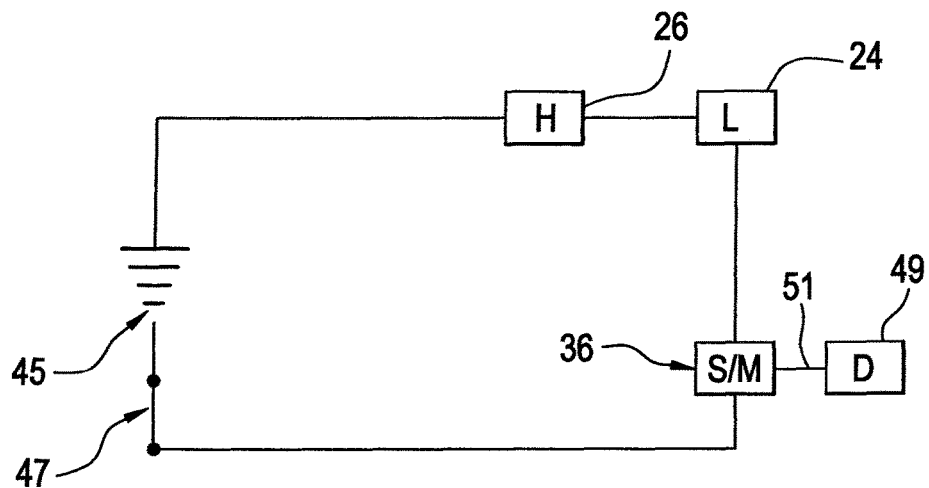
FIG. 5b shows a circuit diagram of one embodiment of circuitry.
Figure 5C:
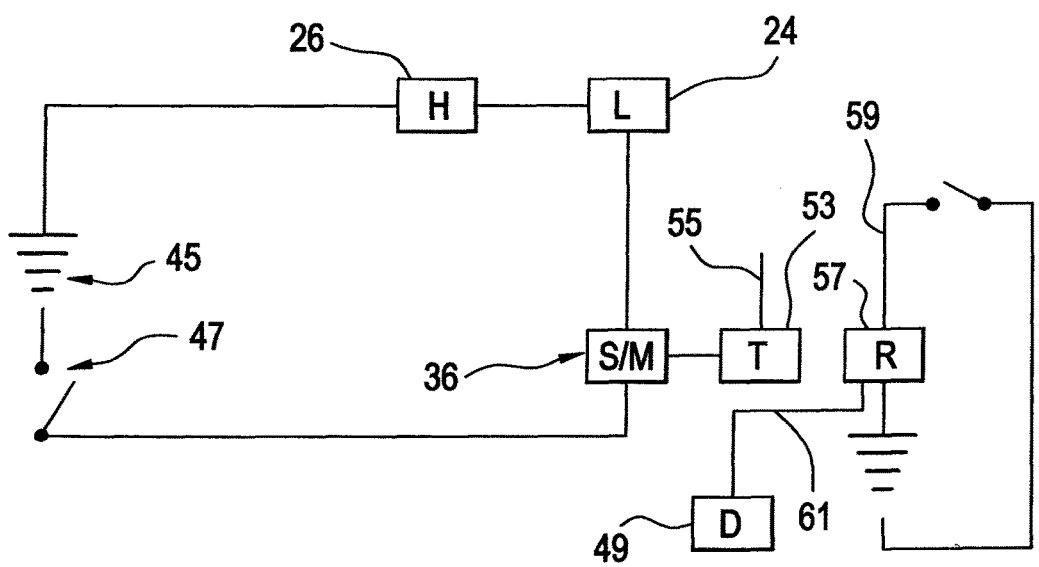
FIG. 5c shows a circuit diagram of a second embodiment of circuitry.

With reference to FIGS. 5b and 5c, two examples of electrical circuitry usable in connection with the present invention are schematically shown. With reference to FIG. 5b, a source of power is schematically shown referred to by reference numeral 45. This may comprise a battery contained within the mouthpiece 10 or, alternatively, the source of power remotely located and connected via the conductor 20 (FIGS. 1 and 2). In either event, an on-off switch 47 controls activation and deactivation of the system. In FIGS. 5b and 5c, the heating resistors 26 and LED 24 are schematically shown. Reference numeral 36 refers to a combination sensor microprocessor while the associated display is referred to with reference numeral 49. In the circuit of FIG. 5b, the microprocessor is connected to the display via a hard wired electrical conductor 51. In the embodiment of FIG. 5c, the microprocessor is connected to a transmitter 53 which has an antenna 55 that transmits signals corresponding to the pH via the antenna 55 to a receiver 57 antenna 59 which then provides the information via a conductor 61 to the display 49.

With reference to FIGS. 6-17, the manner of operation of the present invention in its preferred mode of operation will now be described.

Figure 6:
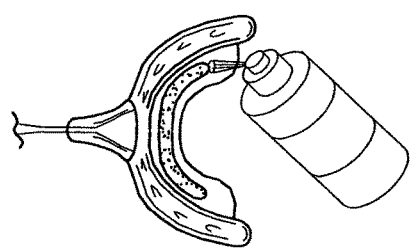
FIGS. 6-17 show the sequence of intended operation of the inventive mouthpiece.
Figure 7:
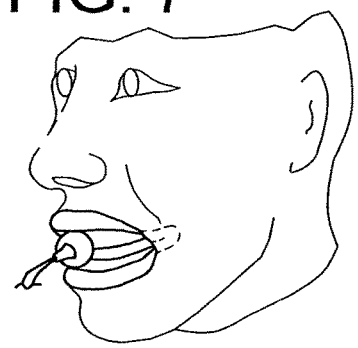

With reference to FIG. 6, gel from a canister thereof is applied to the upper and lower areas of the mouthpiece 10 above and below the bite surface 12. With reference to FIG. 7, the mouthpiece is inserted into the mouth and the LEDs 24 and heat resistors 26 are activated.

Figure 8:
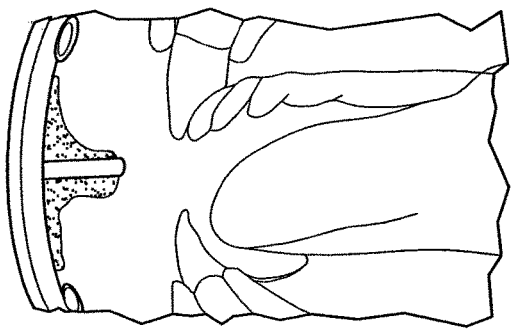
Figure 9:
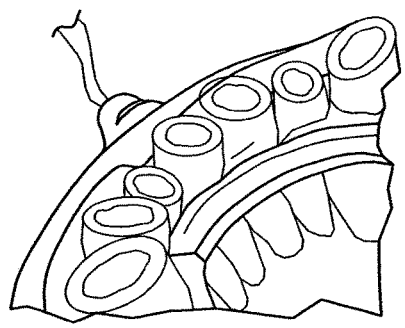

With reference to FIGS. 8 and 9, the peripheral bead 18 of the mouthpiece 10 creates a seal at the margin between the teeth and gums so that the oral cavity of the user is completely sealed off from the outside environment.

Figure 10:
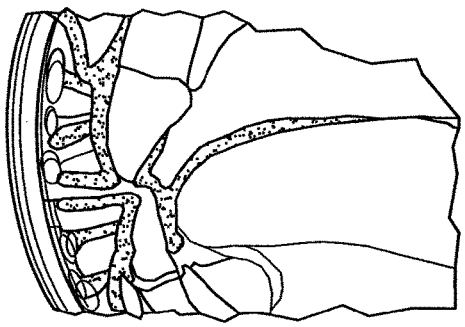
Figure 11:
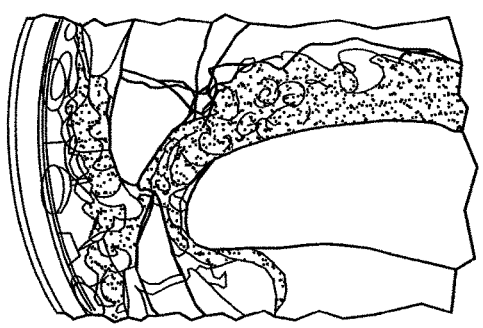
Figure 12:
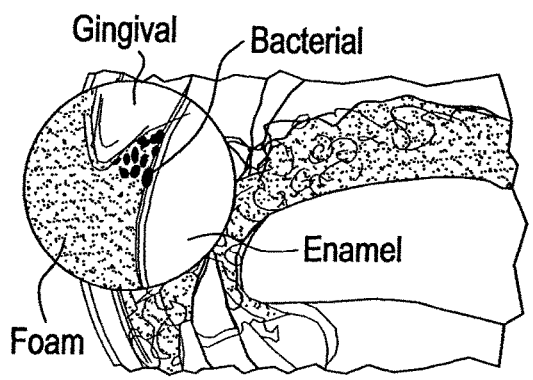
Figure 13:
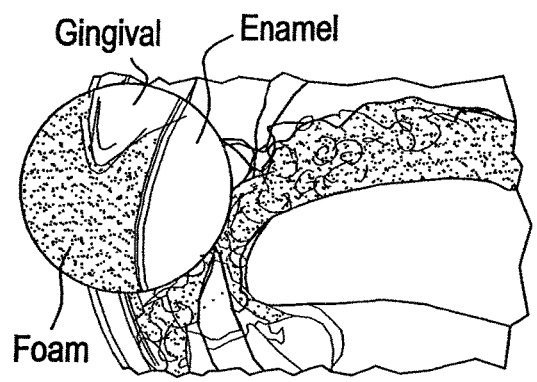
Figure 14:
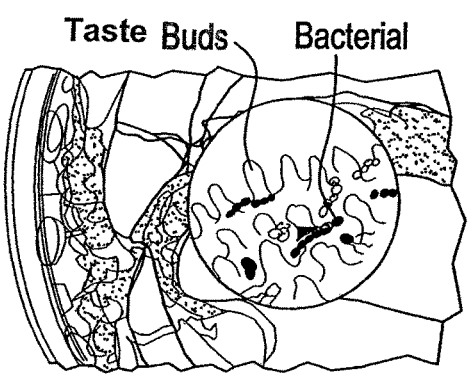
Figure 15:
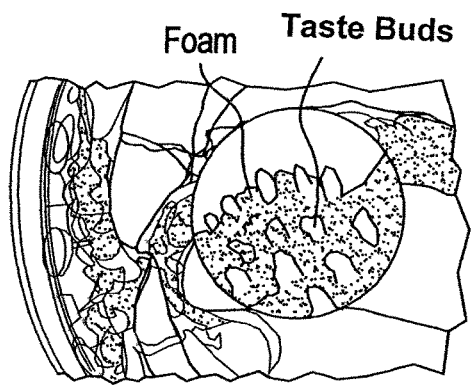
Figure 16:
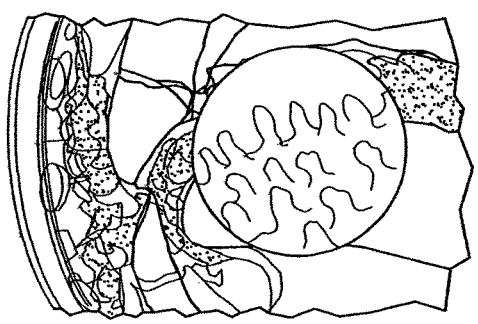
Figure 17:
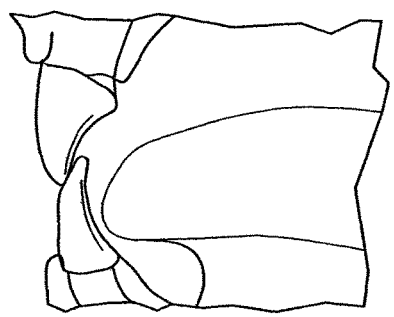

With reference to FIGS. 10-11, when the temperature of the oral cavity rises above a threshold temperature, typically over 100 degrees F., the gel quickly transforms into foam and expands over the teeth, gums, roof of the mouth, tongue, and other areas and interstices of the oral cavity.

With reference to FIGS. 12-15, the foam kills off undesirable bacteria from the tooth enamel, tongue, and other oral cavity surfaces. As a result, the tongue, teeth, and oral cavity are cleansed of harmful bacteria and the pH of the oral cavity rises to the healthy range of 6.75 to 7.25. The pH of the oral cavity is continually monitored during the process via the display 27 (FIG. 3) or 49 (FIGS. 5b and 5c). In the display 27, each light corresponds to a unique pH or pH range. Once the pH of the oral cavity has been restored to within the healthy range, the mouthpiece 10 may be deactivated and removed from the mouth and the oral cavity may be rinsed to remove the foam therefrom.

Treatments such as that which is described above may be repeated on a daily basis or multiple times during a day to maintain the pH of the oral cavity within a healthy range to not only enhance the health of the user's oral cavity, but to enhance health generally.

The present invention takes a unique formulation that works in conjunction with the closed system mouthpiece that has heat and light activating the gel to increase volume and change into a foam. This foam can expand against the walls of the oral cavity and push its contents into these dark, oxygen poor areas where the "bad" bacteria thrive. The objective is to change the environment from oxygen poor-low pH loving sites where the pathogenic bacteria thrive to a safer, more effective way to rebalance homeostasis in the mouth towards health.

In the parent application referenced in paragraph [0001] above, co-Applicant Jonathan B. Levine identified preferred formulations for use in conjunction with the invention disclosed therein as follows: Applicants have devised four separate formulations of gels that effectively fulfill the objects and purposes of the present invention. A first formulation includes a mixture of PEG-8, Propylene Glycol, Canola Oil, PVP-Hydrogen Peroxide K-90 (1.7% peroxide), Glycerin, Dimethyl Isosorbide, Poloxamer 407, Ascorbic Acid, Green Tea Extract, *Vitis Vinifera* (Grape Seed) Extract, Sodium Bicarbonate, Flavor, Xylitol, and Aqua. A second formulation includes a mixture of PEG-8, Propylene Glycol, Canola Oil, PVP-Hydrogen Peroxide K-30 (1.7% peroxide), Glycerin, Dimethyl Isosorbide, Poloxamer 188, Xylitol, Ascorbic Acid, Green Tea Extract, *Vitis Vinifera* (Grape Seed) Extract, Flavor, and Aqua. A third formulation includes a mixture of PEG-8, Propylene Glycol, Canola Oil, Glycerin, PVP-Hydrogen Peroxide K-90, Dimethyl Isosorbide, PVP-Hydrogen Peroxide K-30, Xylitol, Poloxamer 188, Flavor, Potassium Olivoyl Hydrolyzed Oat Protein, Sorbitol, Tocopheryl Acetate, Tetrahexyldecyl Ascorbate, Green Tea Extract, *Vitis Vinifera* (Grape Seed) Extract, Aqua, Mica, Titanium Dioxide, Sodium Bicarbonate, Hydrogenated Cotton Seed Oil, and Potassium Chloride. A fourth formulation includes a mixture of PEG-8, Propylene Glycol, Canola Oil, Glycerin, PVP-Hydrogen Peroxide K-90, PVP-Hydrogen Peroxide K-30, Fumed Silica (Vendor #2), Dimethyl Isosorbide, Potassium Olivoyl Hydrolyzed Oat Protein, *Stevia* Glucosides, Tocopheryl Acetate, Hydrogenated Cotton Seed Oil, Tetrahexyldecyl Ascorbate, Xylitol, Flavor (Flavorchem), Sorbitol, Aqua, Sodium Bicarbonate, Potassium Chloride, Mica, and Titanium Dioxide. In the present application, the specifics concerning preferred formulations including identification of mandatory and optional ingredients, the proportions of the ingredients in the mixture, range percentages, the functions of each ingredient, and the manner of preparing the formulations are all disclosed in detail.

The inventive formulation is preferably created in the following manner.

Maintaining a minimum pH of 7.5 throughout the shelf life of the formulation (post foaming gel) is critical to its effectiveness. In addition to the pH buffering agents, the preparation of the equipment prior to manufacture and filling, component specifications (primary container), manufacturing conditions, and post manufacturing handling of the finished product are also important factors in the process. Each will be discussed separately.

Component (primary container) Specifications:

Components are filled into an Aptar Bag-On-Valve (BOV) which has been modified through the addition of FDA food grade gaskets (BUNA) and use of a Nitronic valve spring in lieu of a standard stainless steel spring. These changes, especially the Nitronic spring, are less reactive with the Hydrogen Peroxide in the formula and reduce the rate of decomposition and subsequent reduction of pH. The formula is very viscous so use of a female BOV is recommended. The secondary container, a 45 mm×165 mm Aluminum Tube does not contact the formula in any way.

The equipment utilized to manufacture the formulation must be at a minimum 304 grade stainless steel. This includes equipment and utensils used for weighing, compounding & mixing, and filling & packaging the product. The preparation and cleaning of this equipment prior to initiating the process is critical to minimizing the probability for contamination and degradation of the product. Preparation steps are:

- Submersion or contact with a degreasing agent such as a 10%-15% solution of Oakite 33 for a minimum of thirty minutes. This should be followed by a complete rinse of the equipment with deionized water until the effluent is pH neutral.
- Submersion or contact with an acid solution consisting of 70%-80% Nitric Acid and 20%-30% Hydrofluoric Acid for a minimum of thirty minutes. This should be followed by a complete rinse of the equipment with deionized water until the effluent is pH neutral.
- Submersion or contact with 100% Nitric Acid for a minimum of thirty minutes. This should be followed by a complete rinse of the equipment with deionized water until the effluent is pH neutral.
- Submersion or contact with a 5% solution of Hydrogen Peroxide for a minimum of thirty minutes. This should be followed by a complete rinse of the equipment with deionized water until the effluent is pH neutral.
- The equipment should now be completely cleaned and passivated so no "free metal ions" are available to catalyze the decomposition of the formula.

The manufacture of the bulk concentrate of the formulation must be completed in a suitably sized mixing tank (for the quantity of product desired) and equipped as follows:

- Variable speed counter rotating sweep agitation with side Teflon scrapers.
- Variable speed propeller agitation for rapidly mixing powers into solution.
- Cone shaped bottom with ball valve.
- Recirculation loop so that product can be pumped from the bottom of the tank to the top of the batch.
- Positive displacement pump.
- Top opening hatch to facilitate introduction of ingredients.
- Capability of nitrogen purging on top of batch.
- Heating/Cooling Capabilities.

The sequence of ingredient additions and mixing for a formulation including all mandatory and optional ingredients should be as follows with a Nitrogen flush (blanket) being constantly maintained on the batch:

1. Add Sorbitol Solution, Propylene Glycol and $1^{st}$ DI Water addition. Turn on sweep agitation and adjust from 10-15 rpm. Turn on propeller agitation and adjust from 200-400 rpm.
2. Slowly add PVP K90 to the Main Tank and mix until dissolved.
3. Add PEG 300 to the Main Tank and begin heating the contents to 45°-50° C.
4. At 45°-50° C. add Pluracare F-68 to the Main Tank and mix until dissolved then turn off heating.
5. At 45°-50° C. add Menthol to the Main Tank and mix until dissolved.
6. In a suitably sized container dissolve Sodium Hydroxide, Sodium Bicarbonate, Sodium Silicate Pentahydrate and EDTA in the $2^{nd}$ DI Water addition. When all ingredients are dissolved add the premix to the Main Tank.
7. In a suitably sized container dissolve Cetylpyridium Chloride and Xylitol with the $3^{rd}$ DI Water addition. When all ingredients are dissolved add the premix to the Main Tank.
8. When the temperature of the Main Tank is below 40° C. add Vitamin E.
9. In a suitable sized container dissolve BHT with Wintermint Flavor. When all ingredients are dissolved add the premix to the Main Tank.
10. In order, add Arasolve DMI, Magnasweet, and Olivoyl Avenate Surfactant to the Main Tank. Continuing mixing until the batch is uniform.
11. Slowly add the Proxydone XL-10 to the Main Tank and continue mixing until uniform.
12. Slowly add the Aerosil 200 Pharam to the Main Tank.
13. Continue mixing for a minimum of one hour or until all powders are dissolved.
14. Turn off propeller agitation/continue sweep mixing for an additional hour at 5-10 rpm.
15. Sample the batch (top and bottom) for laboratory analysis.

The formulation is a non-Newtonian fluid with a viscosity between 70,000 cps-95,000 cps. To properly fill the bulk concentrate into a BOV the sweep mixing should be maintained at 10-15 rpm throughout the filling process so that the product remains as fluid as possible. Critical filling are as follows:

1. Premix the formula amount of isopentane with the bulk concentrate. This is accomplished through the use on a metering pump and blending ribbons which are all under pressure.
2. Put nitrogen gas around the outside of the BOV at a pressure of 42-45 psig and hermetically seal the valve of the BOV to the aluminum can.
3. Fill the desired amount of product into the BOV by pressure filling through the valve at a pressure between 400-500 psig.
4. Remove any residual product from the opening in the valve cup.
5. Do not subject the can to heating in a hot water bath.

The post manufacturing handling of the formulation is a critical step in the process. The following steps should be followed:

1. Immediately after the final packaging of the product is completed the product is placed in refrigerated storage at 36-40° F. The product will remain in refrigerated storage until it is shipped to distribution centers.
2. The product does not have to be shipped under refrigerated conditions but it should be shipped by $2^{nd}$ day air at a minimum.
3. When it is delivered to the distribution centers it should once again be put into refrigeration.
4. During shipment from the distribution centers to dental centers/offices it does not have to be shipped under refrigerated conditions but it should be shipped by $2^{nd}$ day air at a minimum.
5. Dental centers/offices should put the product into refrigeration until provided to the ultimate customer.

The following six examples are provided to demonstrate preferred manners of use of the inventive formulations and to demonstrate their effectiveness.

EXAMPLE 1

Breath Freshening

A 0.1% by weight CPC, 0.306% sodium bicarbonate and 1.3% hydrogen peroxide oral gel composition was formulated by mixing the balance distilled water, 19.4% sorbitol, and 15.5% of a humectant to enhance penetration with sweep and propeller agitations. Then 5.3% by weight polyvinylpyrrodidone K 90 was added and mixed until dissolved. The 4.8% by weight polyethylene glycol 300 was added to the mixture and heated to 45-50° C. At 45-50° C., the 0.9% by weight a general cleansing surfactant was added to the mixture and mixed until dissolved, and the heat was removed following the addition of 0.1% of a suitable flavoring agent to the mixture. In a separate container, 0.03% of a strong base, 0.306% sodium bicarbonate, 0.2% of a pH stabilizer, and 0.15% of EDTA were combined and dissolved in distilled water. This phase was then added to the main mixture. In another separate container, 0.1% by weight CPC and 1.3% by weight xylitol were combined and dissolved with distilled water, and then added to the previous mixture. Thereafter, once the mixture had cooled to below 40° C., 0.1% of an antioxidant was added to the mixture. In another separate container, 0.1% by weight a preservative and 1.3% by weight suitable flavoring agent were dissolved and then added to the previous mixture until dissolved. To the main mixture, the following were added in sequence: 0.5% an additional humectant to enhance penetration, 0.5% flavoring agent and 1.0% of an emollient, and mixed until uniform. Then, 7.3% peroxydone XL-10 followed by 4.9% aerosol 200 were added to the mixture and mixed until uniform. The composition was mixed for a minimum of one hour by propeller agitation, followed by an additional hour minimum of sweep agitation. Following mixing and prior to filling, 3.0% by weight isopentane was premixed with the bulk concentrate. This formulation was coated onto the rear-facing surfaces of a mouthpiece containing heat and light components. The mouthpiece was then inserted into the mouth of a user and the heat and light components were activated. At 37° C., the formulation began to foam and filled the oral cavity as the temperature increased over 40° C. The pH of the oral cavity was monitored and became 7.0 after 8 minutes of treatment. Thereafter, the mouthpiece was removed and the oral cavity rinsed. This procedure eliminated halitosis from the oral cavity.

EXAMPLE 2

Gum Health

A 1.0% by weight CPC, 0.3% sodium bicarbonate and 1.3% hydrogen peroxide oral gel composition was formulated by mixing the balance distilled water, 19.4% sorbitol and 15.5% of a humectant to enhance penetration with sweep and propeller agitations. Then 5.3% by weight polyvinylpyrrodidone K 90 was added and mixed until dissolved. The 4.8% by weight polyethylene glycol 300 was added to the mixture and heated to 45-50° C. At 45-50° C., the 0.9% by weight a general cleansing surfactant was added to the mixture and mixed until dissolved, and the heat was removed following the addition of 0.1% of a flavoring agent to the mixture. In a separate container, 0.03% of a strong base, 0.3% sodium bicarbonate, 0.2% of a pH stabilizer and EDTA were combined and dissolved in distilled water. This phase was then added to the main mixture. In another separate container, 1.0% by weight CPC and 1.3% by weight xylitol were combined and dissolved with distilled water, and then added to the previous mixture. Thereafter, once the mixture had cooled to below 40° C., 0.1% of an antioxidant was added to the mixture. In another separate container, 0.1% by weight a preservative and 1.3% by weight flavoring were dissolved and then added to the previous mixture until dissolved. To the main mixture, the following were added in sequence: 0.5% an additional humectant to enhance penetration, 0.5% flavoring agent and 1.0% of an emollient, and mixed until uniform. Then, 7.3% peroxydone XL-10 followed by 4.9% aerosol 200 were added to the mixture and mixed until uniform. The composition was mixed for a minimum of one hour by propeller agitation, followed by an additional hour minimum of sweep agitation. Following mixing and prior to filling, 3.0% by weight isopentane was premixed with the bulk concentrate. This formulation was coated onto the rear-facing surfaces of a mouthpiece containing heat and light components. The mouthpiece was then inserted into the mouth of a user and the heat and light components were activated. At 37° C., the formulation began to foam and filled the oral cavity as the temperature increased over 40° C. The pH of the oral cavity was monitored and became 7.0 after 8 minutes of treatment. The treatment regimen was repeated daily over a 45-day period. Thereafter each application, the mouthpiece was removed and the oral cavity rinsed. This procedure improved oral soft tissue quality, reduced gingival pocket depth and altered bacterial presence from the oral cavity.

EXAMPLE 3

Teeth Whitening

A 0.1% by weight CPC, 0.3% sodium bicarbonate and 2.0% hydrogen peroxide oral gel composition was formulated by mixing the balance distilled water, 19.4% sorbitol and 15.5% of a humectant to enhance penetration with sweep and propeller agitations. Then 5.3% by weight polyvinylpyrrodidone K 90 was added and mixed until dissolved. The 4.8% by weight polyethylene glycol 300 was added to the mixture and heated to 45-50° C. At 45-50° C., the 0.9% by weight a general cleansing surfactant was added to the mixture and mixed until dissolved, and the heat was removed following the addition of 0.1% of a flavoring agent to the mixture. In a separate container, 0.03% of a strong base, 0.3% sodium bicarbonate, 0.2% of a pH stabilizer, and 0.15% EDTA were combined and dissolved in distilled water. This phase was then added to the main mixture. In another separate container, 0.1% by weight CPC and 1.3% by weight xylitol were combined and dissolved with distilled water, and then added to the previous mixture. Thereafter, once the mixture had cooled to below 40° C., 0.1% of an antioxidant was added to the mixture. In another separate container, 0.1% by weight a preservative and 1.3% by weight flavoring were dissolved and then added to the previous mixture until dissolved. To the main mixture, the following were added in sequence: 0.5% an additional humectant to enhance penetration, 0.5% flavoring agent and 1.0% of an emollient, and mixed until uniform Then, 7.3% peroxydone XL-10 followed by 4.9% aerosol 200 were added to the mixture and mixed until uniform. The composition was mixed for a minimum of one hour by propeller agitation, followed by an additional hour minimum of sweep agitation. Following mixing and prior to filling, 3.0% by weight isopentane was premixed with the bulk concentrate. This formulation was coated onto the rear-facing surfaces of a mouthpiece containing heat and light components. The mouthpiece was then inserted into the mouth of a user and the heat and light components were activated. At 37° C., the formulation began to foam and filled the oral cavity as the temperature increased over 40° C. The pH of the oral cavity was monitored and became 7.0 after 8 minutes of treatment. The treatment regimen was repeated daily over a 45-day period. Thereafter each application, the mouthpiece was removed and the oral cavity rinsed. This procedure enhanced tooth whitening by an average of several shades.

EXAMPLE 4

Breath Freshening

A 0.1% by weight CPC, 0.3% sodium bicarbonate and 1.3% hydrogen peroxide oral gel composition was formulated by mixing the balance distilled water (32.57%), 19.4% sorbitol, 15.5% propylene glycol with sweep and propeller agitations. Then 5.3% by weight polyvinylpyrrodidone K 90 was added and mixed until dissolved. The 4.8% by weight polyethylene glycol 300 was added to the mixture and heated to 45-50° C. At 45-50° C., the 0.9% by weight Poloxamer 188 was added to the mixture and mixed until dissolved, and the heat was removed following the addition of 0.1% by weight menthol to the mixture. In a separate container, 0.03% sodium hydroxide, 0.3% sodium bicarbonate, 0.2% sodium silicate pentahydrate and EDTA were combined and dissolved in distilled water. This phase was then added to the main mixture. In another separate container, 0.1% by weight CPC and 1.3% by weight xylitol were combined and dissolved with distilled water, and then added to the previous mixture. Thereafter, once the mixture had cooled to below 40° C., 0.1% vitamin E was added to the mixture. In another separate container, 0.1% butylated hydroxytoluene and 1.3% flavoring were dissolved and then added to the previous mixture until dissolved. To the main mixture, the following were added in sequence: 0.5% dimethyl isosorbide, 0.5% Mangasweet and 1.0% olivoyl aventate surfactant, and mixed until uniform. Then, 7.3% peroxydone XL-10 (PVP) followed by 4.9% aerosol 200 were added to the mixture and mixed until uniform. The composition was mixed for a minimum of one hour by propeller agitation, followed by an additional hour minimum of sweep agitation. Following mixing and prior to filling, 3.0% by weight isopentane was premixed with the bulk concentrate. This formulation was coated onto the rear-facing surfaces of a mouthpiece containing heat and light components. The mouthpiece was then inserted into the mouth of a user and the heat and light components were activated. At 37° C., the formulation began to foam and filled the oral cavity as the temperature increased over 40° C. The pH of the oral cavity was monitored and became 7.0 after 8 minutes of treatment. Thereafter, the mouthpiece was removed and the oral cavity rinsed. This procedure eliminated halitosis from the oral cavity.

EXAMPLE 5

Gum Health

A 1.0% by weight CPC, 0.3% sodium bicarbonate and 1.3% hydrogen peroxide oral gel composition was formulated by mixing the balance distilled water (31.77%), 19.4% sorbitol, 15.5% propylene glycol with sweep and propeller agitations. Then 5.3% by weight polyvinylpyrrodidone K 90 was added and mixed until dissolved. The 4.8% by weight polyethylene glycol 300 was added to the mixture and heated to 45-50° C. At 45-50° C., the 0.9% by weight Poloxamer 188 was added to the mixture and mixed until dissolved, and the heat was removed following the addition of 0.1% by weight menthol to the mixture. In a separate container, 0.03% sodium hydroxide, 0.3% sodium bicarbonate, 0.2% sodium silicate pentahydrate and EDTA were combined and dissolved in distilled water. This phase was then added to the main mixture. In another separate container, 1.0% by weight CPC and 1.3% by weight xylitol were combined and dissolved with distilled water, and then added to the previous mixture. Thereafter, once the mixture had cooled to below 40° C., 0.1% vitamin E was added to the mixture. In another separate container, 0.1% butylated hydroxytoluene and 1.3% flavoring were dissolved and then added to the previous mixture until dissolved. To the main mixture, the following were added in sequence: 0.5% dimethyl isosorbide, 0.5% Mangasweet and 1.0% olivoyl aventate surfactant, and mixed until uniform. Then, 7.3% peroxydone XL-10 (PVP) followed by 4.9% aerosol 200 were added to the mixture and mixed until uniform. The composition was mixed for a minimum of one hour by propeller agitation, followed by an additional hour minimum of sweep agitation. Following mixing and prior to filling, 3.0% by weight isopentane was premixed with the bulk concentrate. This formulation was coated onto the rear-facing surfaces of a mouthpiece containing heat and light components. The mouthpiece was then inserted into the mouth of a user and the heat and light components were activated. At 37° C., the formulation began to foam and filled the oral cavity as the temperature increased over 40° C. The pH of the oral cavity was monitored and became 7.0 after 8 minutes of treatment. The treatment regimen was repeated daily over a 45-day period. Thereafter each application, the mouthpiece was removed and the oral cavity rinsed. This procedure improved oral soft tissue quality, reduced gingival pocket depth and altered bacterial presence from the oral cavity.

EXAMPLE 6

Teeth Whitening

A 0.1% by weight CPC, 0.3% sodium bicarbonate and 2.0% hydrogen peroxide oral gel composition was formulated by mixing the balance distilled water (32.57%), 19.4% sorbitol, 15.5% propylene glycol with sweep and propeller agitations. Then 5.3% by weight polyvinylpyrrodidone K 90 was added and mixed until dissolved. The 4.8% by weight polyethylene glycol 300 was added to the mixture and heated to 45-50° C. At 45-50° C., the 0.9% by weight Poloxamer 188 was added to the mixture and mixed until dissolved, and the heat was removed following the addition of 0.1% by weight menthol to the mixture. In a separate container, 0.03% sodium hydroxide, 0.3% sodium bicarbonate, 0.2% sodium silicate pentahydrate and EDTA were combined and dissolved in distilled water. This phase was then added to the main mixture. In another separate container, 0.1% by weight CPC and 1.3% by weight xylitol were combined and dissolved with distilled water, and then added to the previous mixture. Thereafter, once the mixture had cooled to below 40° C., 0.1% vitamin E was added to the mixture. In another separate container, 0.1% butylated hydroxytoluene and 1.3% flavoring were dissolved and then added to the previous mixture until dissolved. To the main mixture, the following were added in sequence: 0.5% dimethyl isosorbide, 0.5% Mangasweet and 1.0% olivoyl aventate surfactant, and mixed until uniform. Then, 7.3% peroxydone XL-10 (PVP) followed by 4.9% aerosol 200 were added to the mixture and mixed until uniform. The composition was mixed for a minimum of one hour by propeller agitation, followed by an additional hour minimum of sweep agitation. Following mixing and prior to filling, 3.0% by weight isopentane was premixed with the bulk concentrate. This formulation was coated onto the rear-facing surfaces of a mouthpiece containing heat and light components. The mouthpiece was then inserted into the mouth of a user and the heat and light components were activated. At 37° C., the formulation began to foam and filled the oral cavity as the temperature increased over 40° C. The pH of the oral cavity was monitored and became 7.0 after 8 minutes of treatment. The treatment regimen was repeated daily over a 45-day period. Thereafter each application, the mouthpiece was removed and the oral cavity rinsed. This procedure enhanced tooth whitening by an average of several shades.

The invention defines a mouthpiece that uses light and heat in a closed system and a peripheral seal that works in conjunction with a formulation that transforms from a gel to a foam upon application of heat. Once the foam expands into a closed system, the gasket effect of the closed container seals all contents and optimizes the formulation's effect. The gasket seal 3, 5 gives an additional layer of protection to prevent oxygen escape at the periphery of the mouthpiece where it meets the soft tissue of the gums and the lips.

There is a desire to change the pH of the mouth with a formulation that deodorizes the mouth and oxygenates the teeth and gums thereby decreasing the population of the anaerobic gram negative bacteria that causes gum disease, bad breath and tooth sensitivity. By raising the pH, the acid producing bacteria of decay will also be arrested in this more favorable environment.

As such, an invention has been disclosed in terms of a preferred embodiment thereof as well as a preferred manner of use, that fulfill each and every one of the objects of the invention as set forth hereinabove, and provide a new, useful and unobvious closed system mouthpiece with light and heat generation to activate a formulation to increase its volume, of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. A post foaming gel formulation in the form of a gel that transforms into an expanded foam when heated to within a desired temperature range, comprising a mixture of, by weight, 0.1%±2% Cetylpyridinium Chloride (CPC), 1.3%±2% hydrogen peroxide, 19.4%±2% sorbitol, 15.5%±2% of a penetration agent-humectant, 5.3%±2% polyvinylpyrrolidone K90 (PVP K90), 4.8%±2% polyethylene glycol 300, 0.9%±2% of a general cleansing surfactant, 0.03%±2% of a base pH raiser, 0.3%±2% of sodium bicarbonate, 0.2%±2% of a pH stabilizer, 0.15%±2% Tetrasodium EDTA, 1.3%±2% of a sweetening agent-humectant, 0.1%±2% of an antioxidant, 0.1%±2% of a preservative, 1.3%±2% of a flavoring agent, 0.5%±2% of a further penetration agent-humectant, 1%±2% of an emollient, 7.3%±2% plasdone hydrogen peroxide complex, 4.9%±2% silicon dioxide thickening agent, 3%±2% isopentane, and the balance water.

2. The formulation of claim 1, wherein said desired temperature range includes at least 37° C.

3. The formulation of claim 1, wherein said penetration agent-humectant comprises Propylene Glycol.

4. The formulation of claim 1, wherein said general cleansing surfactant comprises Poloxamer 188.

5. The formulation of claim 1, wherein said base pH raiser comprises Sodium Hydroxide.

6. The formulation of claim 1, wherein said pH stabilizer comprises Sodium Silicate Pentahydrate.

7. The formulation of claim 1, wherein said sweetening agent-humectant comprises Xylitol.

8. The formulation of claim 1, wherein said preservative comprises Butylated Hydroxytoluene (BHT).

9. The formulation of claim 1, wherein said further penetration agent-humectant comprises dimethyl isosorbide.

10. The formulation of claim 1, wherein said emollient comprises potassium olivoyl hydrolyzed oat protein.

11. The formulation of claim 1, further including 0.110%±2% Menthol.

12. The formulation of claim 1, coated onto a mouthpiece and inserted into an oral cavity of a user.

13. The formulation of claim 12, heated to a temperature of at least 37° C. and transformed into an expanded foam.

14. The formulation of claim 2, coated onto a mouthpiece and inserted into an oral cavity of a user.

15. The formulation of claim 12, wherein said mouthpiece has a peripheral seal that seals off said oral cavity.

16. A post foaming gel formulation in the form of a gel that transforms into an expanded foam when heated to within a desired temperature range, comprising a mixture of, by weight, 0.1%±2% Cetylpyridinium Chloride (CPC), 1.3%±2% hydrogen peroxide, 19.4%±2% sorbitol, 15.5%±2% of Propylene Glycol, 5.3%±2% polyvinylpyrrolidone K90 (PVP K90), 4.8%±2% polyethylene glycol 300, 0.9%±2% of Poloxamer 188, 0.03%±2% of Sodium Hydroxide, 0.3%±2% of sodium bicarbonate, 0.2%±2% of a pH stabilizer comprising Sodium Silicate Pentahydrate, 0.15%±2% Tetrasodium EDTA, 1.3%±2% of Xylitol, 0.1%±2% of an antioxidant, 0.1%±2% of a preservative, 1.3%±2% of a flavoring agent, 0.5%±2% of dimethyl isosorbide, 1%±2% of an emollient, 7.3%±2% plasdone hydrogen peroxide complex, 4.9%±2% silicon dioxide thickening agent, 3%±2% isopentane, and the balance water.

17. The formulation of claim 16, wherein said preservative comprises Butylated Hydroxytoluene (BHT).

18. The formulation of claim 16, wherein said emollient comprises potassium olivoyl hydrolyzed oat protein and further includes 0.110%±2% Menthol.

19. The formulation of claim 16, coated onto a mouthpiece having a peripheral seal inserted into an oral cavity of a user and heated to a temperature of at least 37° C. and transformed into an expanded form.

* * * * *